(12) United States Patent
Anderson et al.

(10) Patent No.: US 9,032,780 B2
(45) Date of Patent: May 19, 2015

(54) DETECTOR WITH INTERCHANGEABLE SAMPLE PROBES

(75) Inventors: Randy Anderson, Westchester, IL (US); JeYong Jin, Vernon Hills, IL (US); Andrea Rella, Geneva, IL (US)

(73) Assignee: Honeywell International Inc., Morristown, NJ (US)

( * ) Notice: Subject to any disclaimer, the term of this patent is extended or adjusted under 35 U.S.C. 154(b) by 91 days.

(21) Appl. No.: 13/432,796

(22) Filed: Mar. 28, 2012

(65) Prior Publication Data

US 2013/0255357 A1    Oct. 3, 2013

(51) Int. Cl.
 *G01N 9/00* (2006.01)
 *G01N 1/22* (2006.01)

(52) U.S. Cl.
 CPC .......... *G01N 1/22* (2013.01); *G01N 2001/2285* (2013.01)

(58) Field of Classification Search
 CPC ............. B01J 2523/00; B01J 2523/828; B01J 2523/41; B60W 2510/1085; B60K 17/10; C04B 41/4537; G01N 29/022
 USPC ........ 73/31.01, 24.06, 25.05, 864.73, 863.81, 73/864.33
 See application file for complete search history.

(56) References Cited

U.S. PATENT DOCUMENTS

| | | | |
|---|---|---|---|
| 2004/0069046 A1* | 4/2004 | Sunshine et al. | 73/23.34 |
| 2006/0206051 A1* | 9/2006 | Hamilton | 604/24 |
| 2011/0283769 A1* | 11/2011 | Bohn et al. | 73/23.2 |
| 2013/0160571 A1* | 6/2013 | Williamson | 73/863.41 |

* cited by examiner

*Primary Examiner* — Peter Macchiarolo
*Assistant Examiner* — Mohammed Keramet-Amircola
(74) *Attorney, Agent, or Firm* — Husch Blackwell LLP

(57) ABSTRACT

A gas detector can be releasibly coupled to one of a group of elongated probes each of the probes includes a detector connecting end and a gas in flow/outflow end. The connecting end includes a helical attaching feature which when coupled to the detector defies a plurality of spaced apart angular locking positions. A locking position is selected in response to a flow of air in an adjacent duct to which the detector is being attached. Where the detector carries an elongated display device, the locking position can be selected so that the display device exhibits a desired presentation.

18 Claims, 7 Drawing Sheets

PEM DUCT MOUNT
BLIND USER INTERFACE VERSION
(SIDE PUSH BUTTON AND LED)

PEM DUCT MOUNT LCD
USER INTERFACE VERSION

TUBE IN ITS FINAL POSITION FOR
VERTICAL FLOW

VENT ORIENTATION FOR VERTICAL FLOW ORIENTATION

TWIST TRAVEL PATH FOR VERTICAL FLOW ORIENTATION

FINAL POSITION FOR HORIZONTAL FLOW ORIENTATION

TWIST TRAVEL PATH FOR HORIZONTAL FLOW ORIENTATION

US 9,032,780 B2

DETECTOR WITH INTERCHANGEABLE SAMPLE PROBES

FIELD

The application pertains to duct mountable ambient condition detectors. More particularly, the application pertains to such detectors which include detachable air sampling probes.

BACKGROUND

Stand alone or system based duct mounted detectors find use in a variety of installations including ventilation and air conditioning ducts which provide fresh air to monitored regions. In such installations, it is useful to monitor concentrations of airborne gases, such as carbon dioxide.

In such ducts, air can be moving in vertical or horizontal directions. Quite apart from the direction of air movement, it is, at times, desirable to orient the detectors, relative to the adjacent region, so that any display devices carried on the detector can be easily read by local personnel.

DETAILED DESCRIPTION

Figure 1:
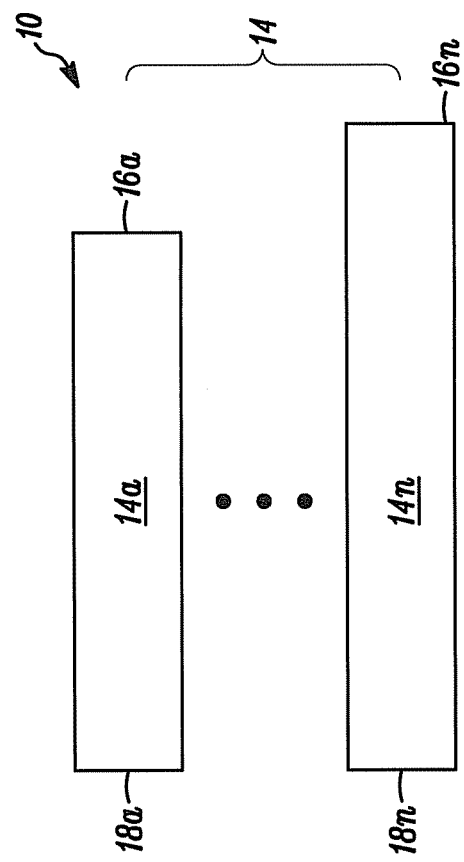
FIG. 1 illustrates an exemplary system in accordance herewith.
Figure 1:
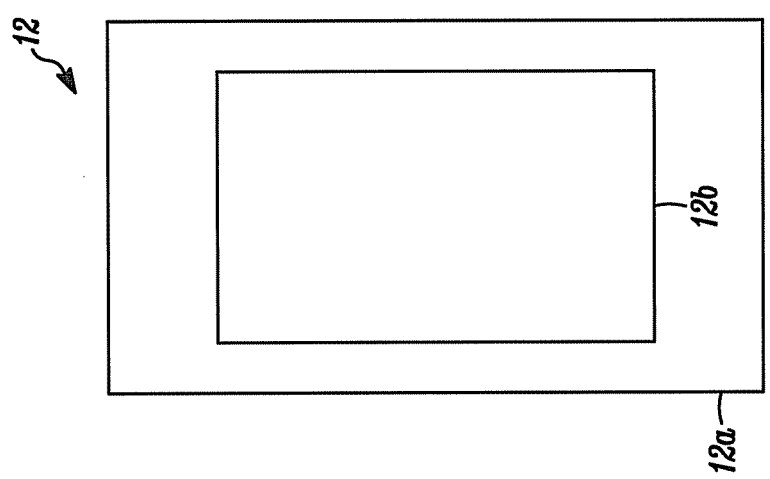

While disclosed embodiments can take many different forms, specific embodiments thereof are shown in the drawings and will be described herein in detail with the understanding that the present disclosure is to be considered as an exemplification of the principles thereof as well as the best mode of practicing same, and is not intended to limit the application or claims to the specific embodiment illustrated.

In embodiments hereof, separate air sampling probes can be releasibly coupled to the detector's body. By selectively orienting the respective probe, inflow and outflow ports of the probe can be oriented to maximize air flowing into the probe and facilitate air flowing from the probe. At the same time, the housing to which the probe is coupled can be independently oriented to provide portrait orientation for a viewer of any display device carried by the housing.

In one aspect, the probe can be formed as an elongated tube with two internal, substantially parallel, channels. One channel extends from a sampling end to a sensing end and provides inflowing air to a sensing region of the detector. A second, parallel, channel provides a parallel path between those ends for air flowing from the sensing region of the detector back into adjacent air flow.

The sampling end can include one or more inflow ports and one or more outflow ports. The inflow and outflow ports are oriented one hundred eighty degrees apart from one another on the tube, relative to a central axis of the tube. One part of a multiple position twist-lock connector can be provided at the sensing end of the probe. The detector can carry a second part of the connector. The probe can be releasibly attached to the detector by the connector with the ports having a selected orientation relative to an air flow being sensed, and where a display on the detector can exhibit a selected orientation for a viewer.

Advantageously, in accordance herewith, various sizes and shapes of probes can be provided. An installer can choose and use an appropriate probe given the characteristics of the ducts to which the detector is being attached.

FIG. 1 illustrates a combination 10 which includes a gas detector 12 and a plurality of attachable probes 14. The detector 12 includes a hollow housing 12a which carries a human readable display device 12b. The device 12b can visually present gas concentrations as well as detector status for maintenance personnel in the vicinity. The housing 12a and display 12b are illustrated with a portrait orientation for ease in viewing.

As those of skill in the art will understand, the probe 14a . . . 14n of the plurality 14 can have different lengths, depending on the characteristics of the respective duct to which the unit is to be attached, or different gas ports adjacent to distal ends 16a . . . 16n. Proximal ends 18a . . . 18n all carry a common coupling element, discussed below, which can rotatably and releasibly mate with housing 12.

Figure 2B:
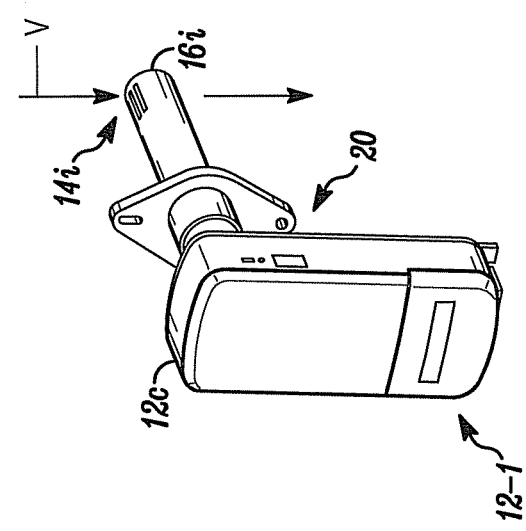
FIG. 2B is a view of another detector and associated probe in accordance herewith.
Figure 2A:
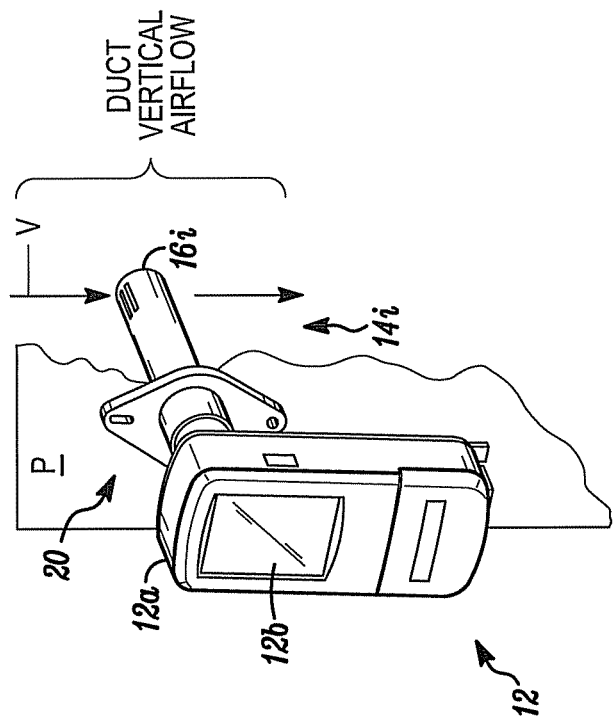
FIG. 2A is a view of one detector and associated probe in accordance herewith.

FIG. 2A illustrates detector 12 mounted on a panel P of a heating or air conditioning duct through which ambient air is flowing in a vertical direction V. The probe 16i extends into the duct to sample the vertically flowing air. The detector 12 is attached to the panel P of the duct by a fastener 20.

FIG. 2B illustrates a detector 12-1, similar to the detector 12 but without the display 12b. The probe 14i, in FIG. 2B extends into the respective duct and is attached thereto by the fastener 20.

Figure 3B:
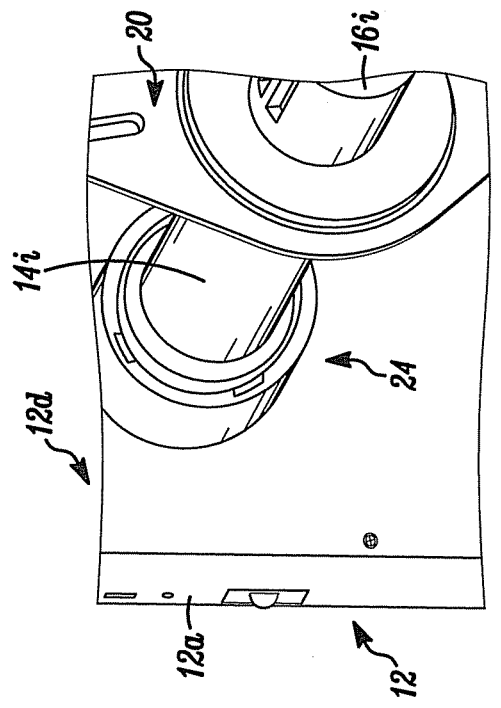
FIG. 3B is an enlargement of the view of FIG. 3A with the probe engaging the housing of the detector.
Figure 3A:
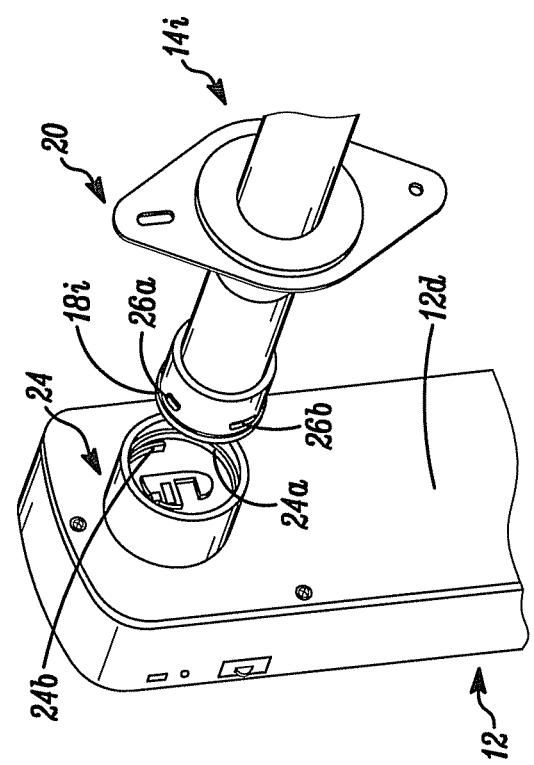
FIG. 3A is a probe side view of the detector and probe of FIG. 1.
Figure 4:
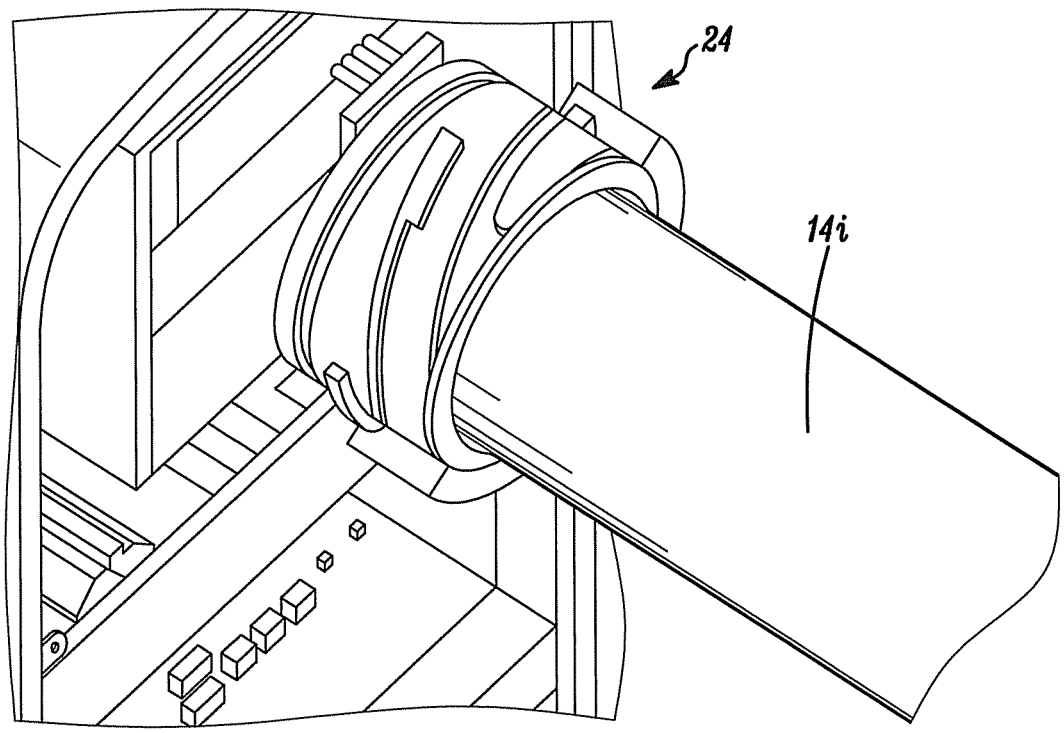
FIG. 4 is an enlarged view of the detector and probe of FIG. 3 where the probe has been locked to the detector with a vertical flow orientation.

As illustrated in FIGS. 3A, B the detector 12 has a rear panel 12d which closes the hollow housing 12. An annular coupling element 24 is carried on the panel 12d. As illustrated in FIGS. 3A, B the proximal end of the probe 14i slidably engages the element 24. The element 24 carries internal helical protrusions 24a which rotatably engage matching external helical patterns, such as 26a, b.

Figure 5B:
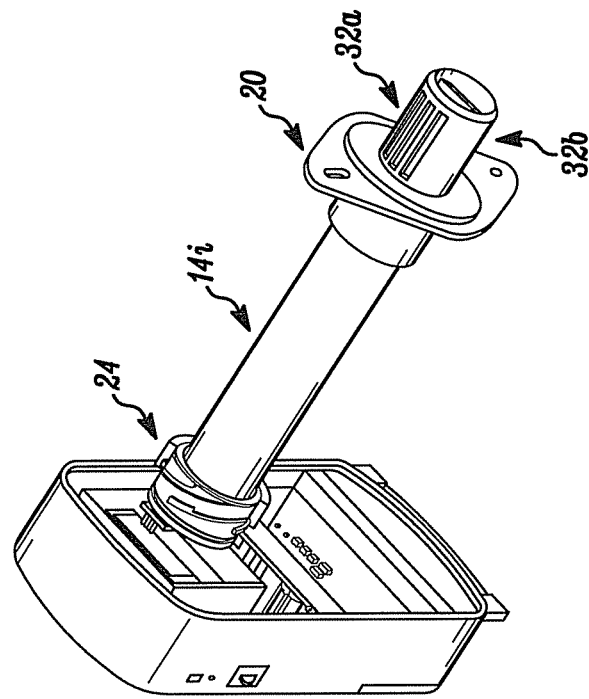
FIG. 5B illustrates the probe of FIG. 5A adjacent to the detector and after rotation with a vertical flow orientation.
Figure 5A:
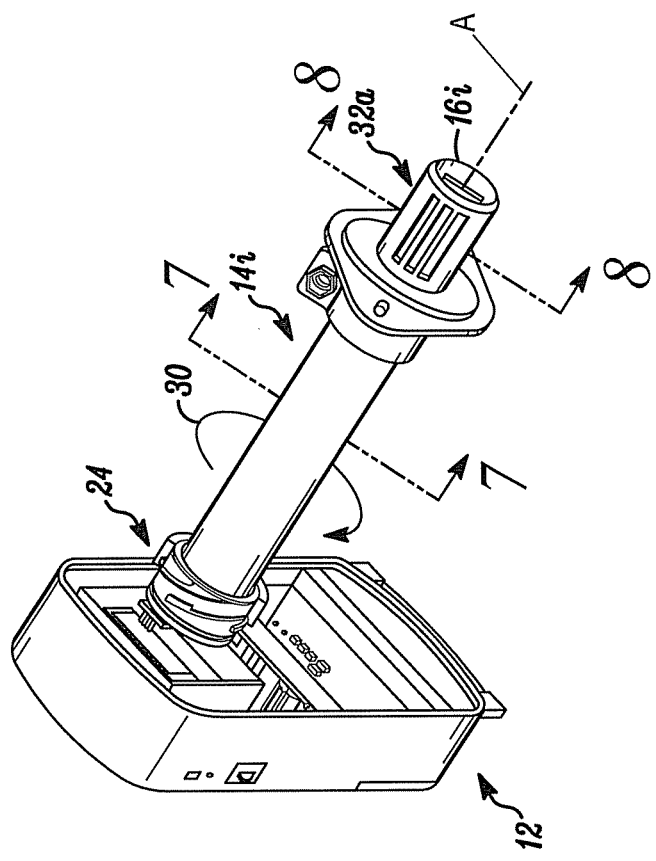
FIG. 5A illustrates the probe of FIG. 4 adjacent to the detector and before rotation.

As the probe 14i engages the connector element 24 while being rotated, in a direction 30 about a central axis A thereof, see FIG. 5A, the helical protrusions 24a and 26a, b slidably and rotatably lock the housing 12 to the proximal end 18i of the probe 14i. A base region 24b of the connector element 24 is located adjacent to a sensing region 36 of the internal gas sensor 38 of the detector 12.

Figure 8:
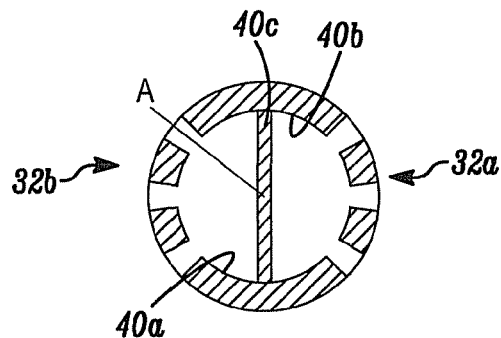
FIG. 8 is a cross-section taken along plane 8-8 of FIG. 9.
Figure 9:
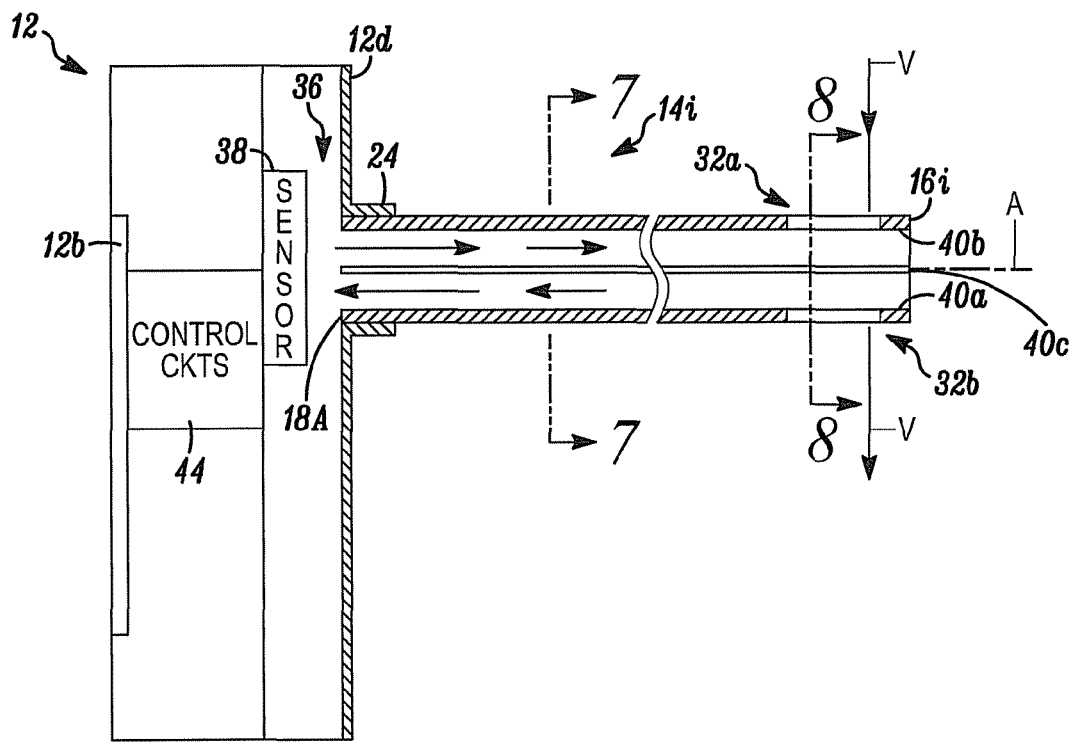
FIG. 9 is a cross-section illustrating additional aspects of the embodiment of FIG. 2A.

The distal ends, such as end 16i of each of the probes 14 are formed with ambient air, including gas or gases of interest, inflow/outflow ports such as 32a, b (best seen in FIGS. 8, 9). The probe, such as 14i, forms an inflow channel 40a, an outflow channel 40b. The channels are separated by a divider 40c which extends along the axis of symmetry A. Ambient air, including the gas(s) of interest travel along channel 40a to the sensing region 36 and sensor 38, and then exit the probe 12i along channel 40b.

Figure 7:
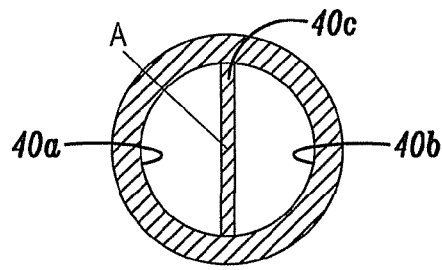
FIG. 7 is a cross-section taken along plane 7-7 of FIG. 9.

FIGS. 7-9 are various cross-sections which illustrate additional aspects of the present apparatus. Control circuits 44 couple the display to the sensor 38 as would be understood by those of skill in the art.

Figure 6B:
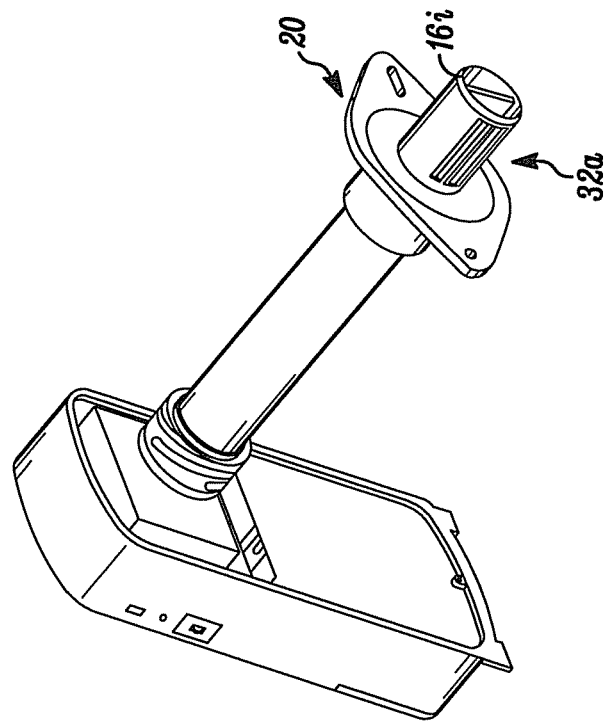
FIG. 6B illustrates the probe of FIG. 6A adjacent to the detector and after rotation with a horizontal flow orientation.
Figure 6A:
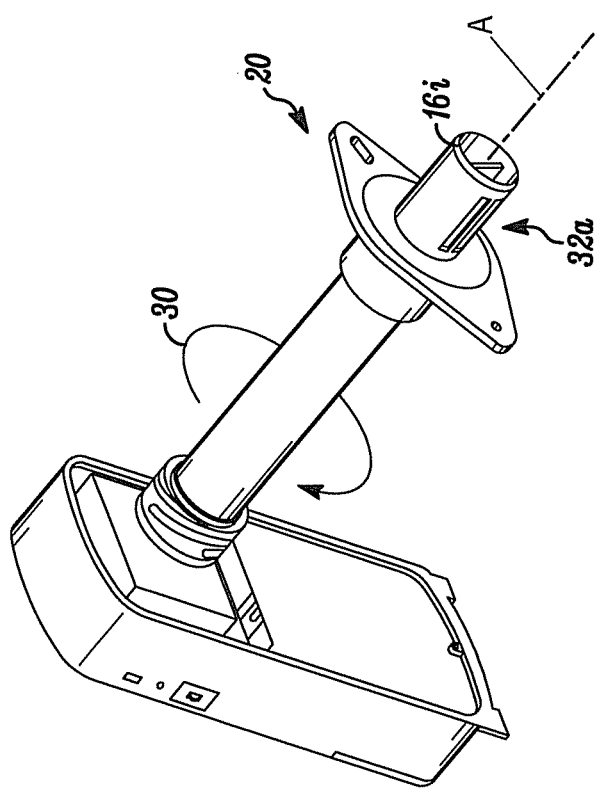
FIG. 6A illustrates the probe of FIG. 2A adjacent to the detector and before rotation thereof.

Because the connector elements 24a and 26a can be arranged to provide a plurality of different starting/ending points for the probe 14i a final position, see FIG. 5B can be provided consistent with a vertical flow, such as the flow V of FIG. 2. Alternately, a final position, see FIG. 6B can be provided consistent with a horizontal flow.

In summary, a respective probe twists and locks to the rear of the enclosure, or housing, via a helix. The helix can be started in one of 4 locations. This option will allow the vent orientation to be vertical or horizontal. The tube also includes a divider. This divider is symmetrical and will permit the sample of duct air to travel to the housing, and sensor, and return to the duct at a constant velocity. The tube has the capability of slowing the speed of the incoming air. The tube completes a closed air circuit from the duct to the sensor and back via three seals. These include, a tube to the ambient room air seal implemented via an axial O-ring; a sensor board to inside the housing sea; and, the collar, carried on the housing for the detector, which prevents the room air from mixing with the duct air.

From the foregoing, it will be observed that numerous variations and modifications may be effected without departing from the spirit and scope hereof. It is to be understood that no limitation with respect to the specific apparatus illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. A detector comprising:
    a housing, the housing carrying a sensor and a display device;
    a first coupling element carried by the housing;
    an input/output probe comprising two internal substantially parallel channels separated by an internal solid divider, which isolates inflowing ambient air from outflowing air and directs the ambient air toward the sensor and outflowing air away from the sensor toward an outflow port;
    a second coupling element carried by the probe,
    where the second coupling element directly and rotatably engages the first coupling element to releasibly couple the probe directly to the housing,
    where the probe directs inflowing ambient air to the sensor in the housing, and, outflowing ambient air from the sensor in the housing, and
    where the sensor is selected from a class which includes a gas sensor, a temperature sensor and a humidity sensor.

2. A detector as in claim 1 where the second coupling element includes a plurality of angularly adjustable locking positions relative to the housing.

3. A detector as in claim 1 which includes an annular seal to isolate duct air from regional air outside of the duct.

4. A detector as in claim 1 with a plurality of dual flow probes each having an elongated hollow body where each of the probes defines parallel inflow and outflow paths which extend from end-to-end of the body.

5. A detector as in claim 2 where the probe has an inflow port and an adjacent outflow port, displaced from the helical feature to provide inflowing ambient air to the sensor in the housing, and, outflowing ambient air from the sensor in the housing.

6. A detector as in claim 5 where the inflow port and the outflow port assume one of a plurality of angular positions relative to the housing, and where the first and second coupling elements include helical coupling elements.

7. A detector as in claim 6 where the housing carries an elongated display and when coupled to a selected probe, the display exhibits a selected orientation.

8. A gas detector comprising:
    a housing, the housing carrying a display device, the housing carrying a gas sensor located adjacent to a sensing region in the housing, the housing defining an inflow/outflow port adjacent to the sensing region with a first part of a locking element carried adjacent to the port; and
    a plurality of dual flow probes each having an elongated hollow body, each of the probes comprising a solid divider defining separate parallel inflow and outflow paths which extend from end-to-end of the body, at least some of the probes having a second part of the locking element,
    where the second part of the locking element directly and rotatably engages the first part of the locking element to releasibly couple a respective probe directly to the housing.

9. A detector as in claim 8 where the second part of the locking element includes a plurality of angular locking positions relative to the housing.

10. A detector as in claim 9 where the second part of the locking element carries a helical locking feature which rotatably engages the first part of the locking element.

11. A detector as in claim 8 where each body has first and second spaced apart ends with one end of each probe carrying the second part of the locking element.

12. A detector as in claim 8 where each body has an inflow/outflow end with spaced apart flow openings.

13. A detector as in claim 12 where the flow openings are spaced angularly about the respective housing.

14. A detector as in claim 13 where the flow openings are spaced ninety degrees apart from each other about the housing.

15. A detector as in claim 13 where the housing carries an elongated display and when coupled to a selected probe, the display exhibits a selected orientation.

16. A detector as in claim 15 where the display is oriented with a portrait orientation.

17. A detector as in claim 8 where each of the probes carries an attachment structure.

18. A detector as in claim 17 where the attachment structure carries an annular seal which excludes ambient atmosphere at a first side of the seal from a second side of the seal.

* * * * *